(12) United States Patent
Terashi et al.

(10) Patent No.: US 8,968,216 B2
(45) Date of Patent: Mar. 3, 2015

(54) MEDICAL GUIDE WIRE

(71) Applicant: FMD Co., Ltd., Toda-shi, Saitama (JP)

(72) Inventors: Tsuyoshi Terashi, Toda (JP); Seiji Shimura, Toda (JP)

(73) Assignee: FMD Co., Ltd, Saitama (JP)

( * ) Notice: Subject to any disclaimer, the term of this patent is extended or adjusted under 35 U.S.C. 154(b) by 0 days.

(21) Appl. No.: 14/289,771

(22) Filed: May 29, 2014

(65) Prior Publication Data

US 2014/0358169 A1    Dec. 4, 2014

(30) Foreign Application Priority Data

May 31, 2013 (JP) .................................. 2013-116146

(51) Int. Cl.
*A61B 5/00* (2006.01)
(52) U.S. Cl.
USPC ........................................................ 600/585
(58) Field of Classification Search
USPC ........................................................ 600/585
See application file for complete search history.

(56) References Cited

U.S. PATENT DOCUMENTS

| | | | |
|---|---|---|---|
| 4,763,647 A | 8/1988 | Gambale | |
| 5,144,959 A | 9/1992 | Gambale et al. | |
| 7,785,273 B2 * | 8/2010 | Eskuri | 600/585 |
| 8,262,588 B2 * | 9/2012 | Miyata et al. | 600/585 |
| 8,608,670 B2 * | 12/2013 | Matsumoto et al. | 600/585 |
| 8,622,932 B2 * | 1/2014 | Matsumoto et al. | 600/585 |
| 8,652,119 B2 * | 2/2014 | Nishigishi | 604/528 |
| 2004/0167442 A1 | 8/2004 | Shireman et al. | |
| 2011/0160703 A1 | 6/2011 | Matsumoto et al. | |
| 2012/0041421 A1 | 2/2012 | Nishigishi | |
| 2012/0323145 A1 | 12/2012 | Nagano et al. | |

FOREIGN PATENT DOCUMENTS

| | | |
|---|---|---|
| JP | 63181774 A | 7/1988 |
| JP | 03-133463 A | 6/1991 |
| JP | 07227429 A | 8/1995 |
| JP | 08-317989 A | 12/1996 |
| JP | 2006519072 A | 8/2006 |
| JP | 2011130976 A | 7/2011 |
| JP | 2012034922 A | 2/2012 |
| JP | 2013000268 A | 1/2013 |

* cited by examiner

*Primary Examiner* — Max Hindenburg
(74) *Attorney, Agent, or Firm* — Sughrue Mion, PLLC

(57) ABSTRACT

An outer coil and an inner coil are joined in parallel with a distal end portion of a core of a guide wire. A winding direction of a strand of the outer coil is the same as that of a strand of the inner coil. Diameters of the outer and inner coils increase or decrease when rotation of the core is transmitted and thereby rotation transmission capability is improved. An outer space wound portion and an inner space wound portion are formed in corresponding positions in the outer coil and the inner coil, respectively, in a core direction. Even if the guide wire has a double-coil structure, the outer and inner space wound portions improve flexibility of the guide wire. A coil pitch of the outer space wound portion differs from a coil pitch of the inner space wound portion. Thereby, engagement of the strands is prevented.

4 Claims, 3 Drawing Sheets

MEDICAL GUIDE WIRE

BACKGROUND OF THE INVENTION

1. Field of the Invention

The present invention relates to a medical guide wire used for treatment of a vascular lesion or the like.

2. Description Related to the Prior Art

Conventionally, a medical guide wire (hereinafter simply referred to as the guide wire) has been used for radial dilation (radial expansion) of a vascular lesion such as a vascular occluded portion or a stenotic portion. The guide wire has a single coil or coaxial inner and outer coils in a distal end portion of a core. The distal end portion of the guide wire is inserted into a blood vessel and advances in the blood vessel until it reaches a lesion. Thereby a radial dilation treatment of the vascular lesion is performed. The radial dilation treatment expands the diameter of the vascular lesion or the like.

The guide wire needs plastic deformation properties and rotation transmission capability to advance in a desired direction in a tortuous blood vessel of complicated structure or at a blood vessel branch. Capability of the guide wire to advance in a desired direction at the blood vessel branch or the like is referred to as the selection capability. The plastic deformation properties represent performance to bend and plastically deform an extreme end portion of the guide wire in a shape of a letter "J" or an inverted letter "J". The rotation transmission capability represents performance of the guide wire to rotate the inserted core and the distal end portion of the guide wire through the coil(s) partially fixed to the core, by rotating a proximal portion (rear end portion) of the guide wire outside of the body.

Japanese Patent Laid-Open Publication No. 08-317989 discloses a guide wire of a double coil structure in which an outer coil is disposed outside of and concentrically with an inner coil through which a core is inserted.

U.S. Pat. No. 5,144,959 (corresponding to Japanese Patent Laid-Open Publication No. 03-133463) discloses a guide wire of a double coil structure with outer and inner coils provided at a distal end of a thin flexible axis. The outer diameter of the inner coil is smaller than the inner diameter of the outer coil.

The Japanese Patent Laid-Open Publication No. 08-317989 only discloses technical principles to improve the rotation transmission capability of the guide wire through the use of a radiopaque member for the inner coil, stainless steel, a shape-memory alloy, or the like for the outer coil, and a resilient member (such as that used for spring) for the core.

The U.S. Pat. No. 5,144,959 only discloses technical principles to improve visual inspection properties in observation mainly in a radiation transmission method. In the U.S. Pat. No. 5,144,959. the inner coil with the outer diameter smaller than the inner diameter of the outer coil is formed of a radiopaque member, in a manner similar to the Japanese Patent Laid-Open Publication No. 08-317989.

Hence, the above-described references do not disclose technical principles for improvements in the rotation transmission capability and the flexibility, owing to winding directions of the outer and inner coils, improvements in the plastic deformation properties, owing to space wound portions provided in corresponding positions at the distal ends of the outer and inner coils, respectively, and improvements in the rotation transmission capability to transmit the rotation to the distal side, owing to a tapered middle portion provided to each of the outer and inner coils and the use of an outer diameter ratio between the maximum outer diameter and the minimum outer diameter, or the like.

SUMMARY OF THE INVENTION

An object of the present invention is to provide a medical guide wire which improves a selection capability at a blood vessel branch and a capability to pass through a lesion.

In order to achieve the above and other objects, the medical guide wire of the present invention comprises a core, an inner coil, an outer coil, an inner space wound portion, and an outer space wound portion. The core has a large diameter on a proximal side. The core is tapered in diameter on a distal side toward a core distal end. The inner coil is formed by helically winding at least one strand. A coil distal end of the inner coil is joined to the core distal end on an outer periphery of a core distal end portion of the core. A coil proximal end of the inner coil is joined to the core distal end portion. The outer coil is formed by helically winding at least one strand. The outer coil is longer than the inner coil in a direction of the core. A coil distal end of the outer coil is joined to the core distal end and a coil proximal end of the outer coil is joined to the core distal end portion in a state that the inner coil is joined to the core. The inner space wound portion is provided on a distal side of the inner coil. The outer space wound portion is provided in the outer coil, which is located outside of the inner space wound portion in a state that the inner and outer coils are joined to the core. A coil pitch of the outer space wound portion differs from the coil pitch of the inner space wound portion. The inner coil has a large constant diameter portion, a tapered middle portion, and a small constant diameter portion from the proximal side to the distal side. The outer coil has a large constant diameter portion, a tapered middle portion, and a small constant diameter portion from the proximal side to the distal side. The space wound portions are provided in coil distal end portions of the small constant diameter portions, respectively. An outer diameter ratio (Di2/Di1) of the inner coil is greater than or equal to 1.15 and less than or equal to 2.80 and an outer diameter ratio (Do2/Do1) of the outer coil is greater than or equal to 1.10 and less than or equal to 1.80 and the outer diameter ratio (Di2/Di1) of the inner coil is greater than the outer diameter ratio (Do2/Do1) of the outer coil {(Di2/Di1)>(Do2/Do1)} where "Di1" denotes an outer diameter of the small constant diameter portion of the inner coil, "Di2" denotes an outer diameter of the large constant diameter portion of the inner coil, "Do1" denotes an outer diameter of the small constant diameter portion of the outer coil, and "Do2" denotes an outer diameter of the large constant diameter portion of the outer coil.

It is preferable that a winding direction of the strand of the inner coil is the same as a winding direction of the strand of the outer coil. Thereby rotation transmission capability of the guide wire to transmit rotation to the distal side is improved. It is preferable that the coil pitch of the inner space wound portion is greater than or equal to 2.00 times a diameter of the strand and less than or equal to 3.50 times the diameter of the strand. It is preferable that the coil pitch of the outer space wound portion is greater than or equal to 1.20 times a diameter of the strand and less than or equal to 1.90 times the diameter of the strand. Thereby engagement of the strands of the inner and outer coils with each other is prevented when the distal end portion of the guide wire is bent and deformed.

It is preferable that at least the large constant diameter portion and the tapered middle portion of the inner coil are close wound portions, in each of which the strands are in contact with each other. It is preferable that a length ratio (LiB/Li) is greater than or equal to 0.70 and less than or equal to 0.96 where "Li" denotes a total length of the inner coil and "LiB" denotes a length of the close wound portion. In the case where the length ratio (LiB/Li) is less than 0.70. the space wound portion is extended. Thereby a torsion angle increases on the proximal side when the proximal side of the core is rotated. Responsivity on the distal side and the rotation transmission capability decrease as the torsion angle increases. When the length ratio (LiB/Li) exceeds 0.96. flexibility of the extreme end portion of the guide wire to be bent in a shape of a letter "J" is reduced and plastic deformation becomes difficult.

According to the present invention, the space wound portions are provided in the corresponding positions at least at the distal ends of the inner coil and the outer coil, respectively. Thereby the distal end portion of the guide wire easily bends in the shape of a letter "J" or an inverted letter "J" and thus the plastic deformation properties are improved. The coil pitch of the inner space wound portion differs from the coil pitch of the outer space wound portion. Thereby the engagement of the strands of the inner and outer coils with each other is prevented when the distal end portion of the guide wire is bent and deformed. The inner coil has the large constant diameter portion, the tapered middle portion, and the small constant diameter portion from the proximal side to the distal side. The outer coil has the large constant diameter portion, the tapered middle portion, and the small constant diameter portion from the proximal side to the distal side. Thereby the rotation transmission capability of the guide wire to transmit the rotation to the distal side is improved. The outer diameter ratio (outer diameter Di2 of the large constant diameter portion/ outer diameter Di1 of the small constant diameter portion) of the inner coil is greater than the outer diameter ratio (outer diameter Do2 of the large constant diameter portion/outer diameter Do1 of the small constant diameter portion) of the outer coil. Thereby, the rotation transmission capability to transmit the rotation to the distal end is further improved. The torsional moment on the inner coil, which is joined to the small-diameter core, is lower than the torsional moment on the outer coil, which is joined to the large-diameter core, in accordance with the difference in diameter between the small-diameter core to which the inner coil is joined and the large-diameter core to which the outer coil is joined. Making the outer diameter ratio of the inner coil greater than the outer diameter ratio of the outer coil compensates for the reduction in the torsional moment on the inner coil. Furthermore, the outer diameter ratio (Di2/Di1) of the inner coil is greater than or equal to 1.15 and less than or equal to 2.80. The outer diameter ratio (Do2/Do1) of the outer coil is greater than or equal to 1.10 and less than or equal to 1.80. Thereby a certain amount of clearance is created between the inner vascular diameter of a body part to be treated and practical dimensions of a medical tool used for the radial dilation treatment.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS (First Embodiment)

Figure 1:
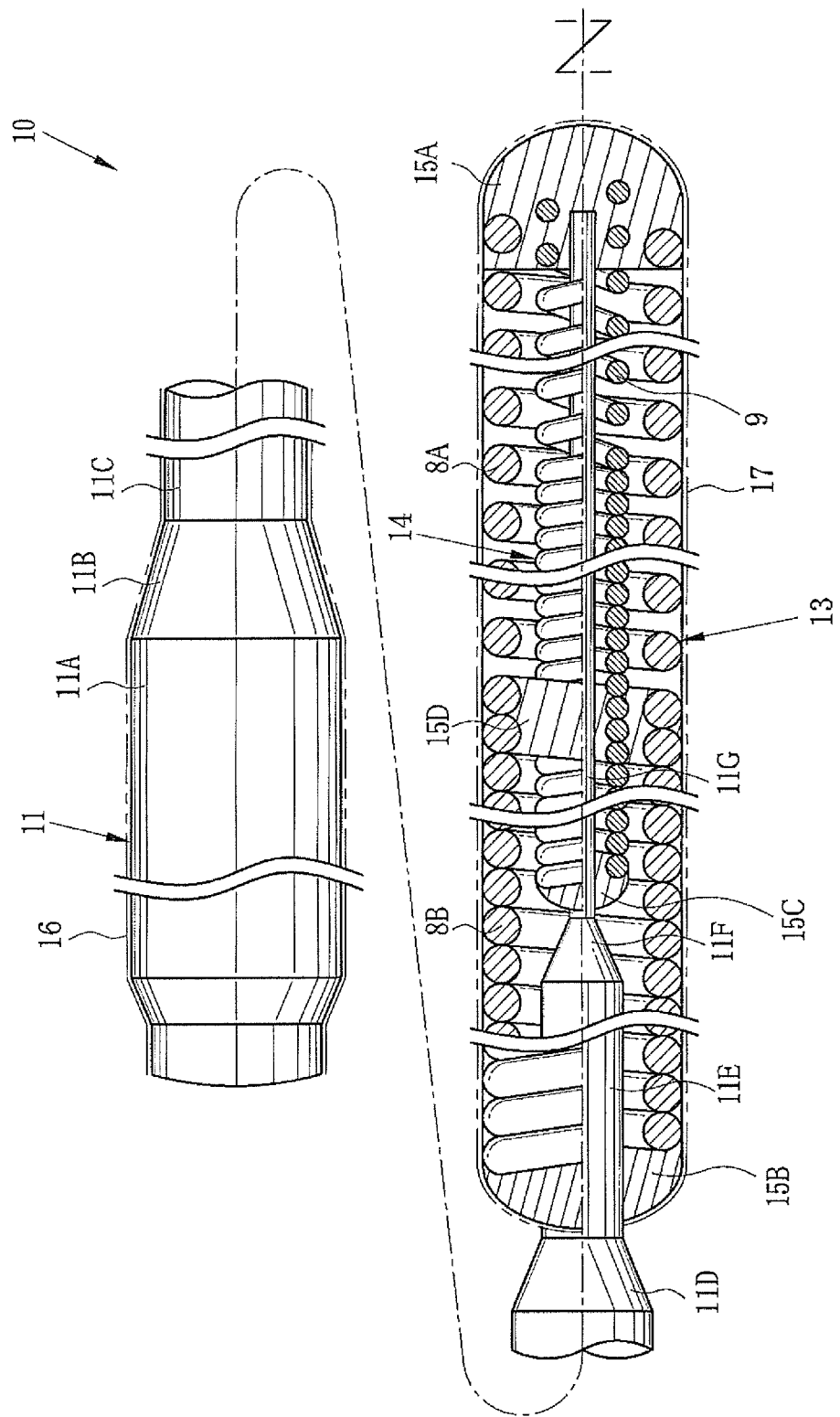
FIG. 1 is a side view illustrating a partially cutaway medical wire according to a first embodiment of the present invention.

As shown in FIG. 1, a guide wire 10 comprises a core 11, an outer coil 13, an inner coil 14, and joining sections 15A, 15B, 15C, and 15D for joining the core 11 and the outer coil 13 and/or the inner coil 14. The core 11 is made from stainless steel or Ni—Ti alloy. The high-strength stainless steel core 11 is manufactured by repeating a wire drawing process and an annealing process as described in Japanese Patent Laid-Open Publication No. 2002-69586. for example. The Ni—Ti alloy core 11 is manufactured by thermal processing under certain conditions as described in Japanese Patent Laid-Open Publication No. 2002-69555. Note that the guide wire 10 according to the present invention has an extremely small diameter relative to its length. The guide wire 10 is partially exaggerated or omitted in drawings because it is difficult to illustrate the guide wire 10 in a specified area if the same scaling is used for horizontal and vertical directions.

The core 11 comprises a first constant diameter portion 11A, a first tapered portion 11B, a second constant diameter portion 11C, a second tapered portion 11D, a third constant diameter portion 11E, a third tapered portion 11F, and a fourth constant diameter portion 11G, in this order from a proximal side. An outer diameter of the core 11 tapers from, for example, 0.3556 mm (that is, 0.014 inches, for cardiovascular treatment) to 0.060 mm, from the proximal side toward a distal side. A fluorocarbon polymer coating 16 is applied to an outer periphery of a large diameter portion on the proximal side of the core 11.

The outer coil 13 is composed of one or more strands 8, which are wound helically into one or more cylindrical shapes. The strand 8 of the outer coil 13 is wound in a direction of "Z-shaped winding" (right-hand thread direction in a shape of a letter "Z"), for example.

The outer coil 13 is joined to the core 11 via the joining section 15A (hereinafter referred to as the distal joining section 15A) and the joining section 15B (hereinafter referred to as the proximal joining section 15B), in a state that the third constant diameter portion 11E, the third tapered portion 11F, and the fourth constant diameter portion 11G of the core 11 are inserted into the wound outer coil 13. The distal joining section 15A has a dome-like shape with a circular cross-section and provided at a distal end of the guide wire 10, for example.

The proximal joining section 15B is provided to the third constant diameter portion 11E. The outer diameter of the third constant diameter portion 11E is greater than or equal to 0.160 mm and less than or equal to 0.190 mm. A hydrophilic polymer coating 17 is applied to an outer periphery of each of the outer coil 13, the distal joining section 15A, and the proximal joining section 15B.

Figure 2:
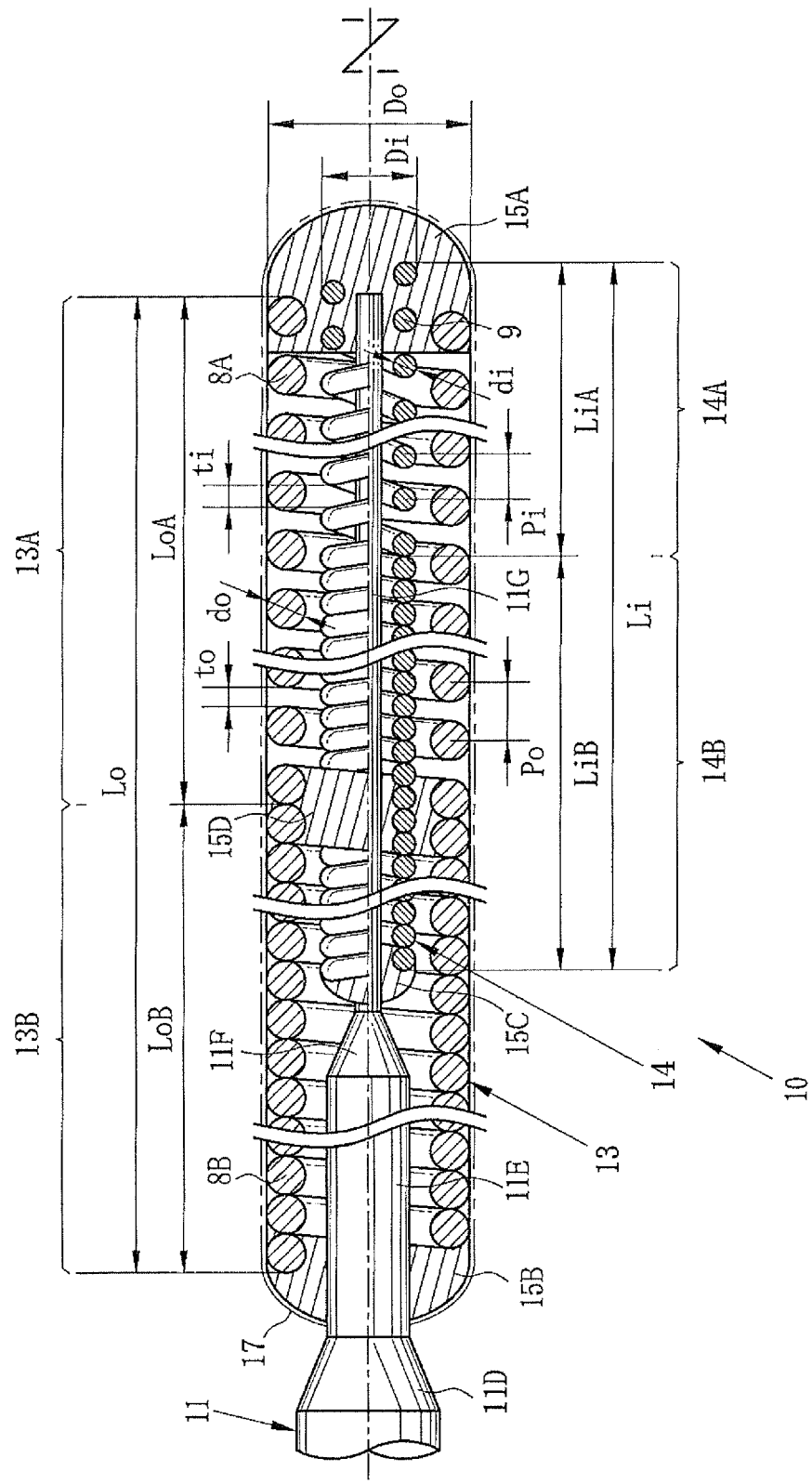
FIG. 2 is cross-sectional view illustrating dimensions of main parts of the medical guide wire according to the first embodiment.

As shown in FIG. 2, an outer diameter "Do" of the outer coil 13 is greater than or equal to 0.300 mm and less than or equal to 0.3556 mm. The length (total length) "Lo" of the outer coil 13 in the core direction is greater than or equal to 100 mm and less than or equal to 300 mm. A diameter "do" of the strand 8 of the outer coil 13 is greater than or equal to 0.055 mm and less than or equal to 0.090 mm.

The outer coil 13 comprises a space wound portion (outer space wound portion) 13A on the distal side and a close wound portion (outer close wound portion) 13B on the proximal side. The outer space wound portion 13A is formed of a radiopaque strand 8A made from platinum, platinum-nickel alloy, tungsten, or the like. The outer close wound portion 13B is formed of a radiolucent strand 8B made from stainless steel or the like.

A length "LoA" of the outer space wound portion 13A is greater than or equal to 20 mm and less than or equal to 60 mm, for example, 40 mm. The outer space wound portion 13A is provided in a region of at least 20 mm, from the inner end of the dome-shaped distal joining section 15A toward the proximal side. A length "LoB" of the outer close wound portion 13B is greater than or equal to 90 mm and less than or equal to 180 mm, for example, 120 mm.

The outer space wound portion 13A and the outer close wound portion 13B are joined with each other via the joining section (hereinafter referred to as the middle joining section) 15D, which is located between the distal end and the proximal end of the core 11. For example, a brazing member such as solder, or the like is used for the middle joining section 15D. A part of the outer space wound portion 13A and a part of the outer close wound portion 13B are tightly joined with each other and the brazing member is applied to the joining portion of the outer space wound portion 13A and the outer close wound portion 13B.

A coil pitch "Po" of the outer space wound portion 13A is greater than or equal to 1.20 times the diameter "do" of the strand 8A and less than or equal to 1.90 times the diameter "do" of the strand 8A. A space "to" between the strands 8A of the outer space wound portion 13A is smaller than the diameter "do" of the strand 8A. In this embodiment, the diameter "do" of the strand 8A is 0.060 mm. The coil pitch "Po" is 1.5 times the diameter "do", that is, 0.090 mm. The space "to" between the strands 8A is 0.030 mm, which is smaller than the diameter "do" (in this case, 0.060 mm) of the strand 8A. The outer close wound portion 13B is longer than or equal to ⅗ of the length of the outer coil 13 in the lengthwise direction. Note that, in the case where the material of the outer space wound portion 13A differs from the material of the outer close wound portion 13B as described in this embodiment, the diameter of the strand 8A may differ from the diameter of the strand 8B. In this case, for example, the diameter "do" of the strand 8A is 0.060 mm and the diameter of the strand 8B is 0.055 mm.

The inner coil 14 is composed of one or more strands 9, which are wound into one or more cylindrical shapes. The strand 9 is made from the stainless steel or the Ni—Ti alloy, as with the core 11, or the tungsten or the like. The strand 9 is preferably made from the stainless steel. The strand 9 of the inner coil 14 is wound in the same direction as that of the outer coil 13. In the case where the outer coil 13 is wound about the core 11 into the "Z" shape, the inner coil 14 is also wound into the "Z" shape.

The inner coil 14 is provided between the outer coil 13 and the fourth constant diameter portion 11G. A total length "Li" of the inner coil 14 is shorter than the total length of the outer coil 13. The inner coil 14 is joined concentrically with the outer coil 13. The inner coil 14 is joined to the core 11 via the distal joining section 15A and the joining section (hereinafter referred to as the proximal joining section) 15C that is located on the proximal side of the core 11, in a state that the fourth constant diameter portion 11G is inserted into the inner coil 14. The proximal joining section 15C is provided to the fourth constant diameter portion 11G having the outer diameter greater than or equal to 0.100 mm and less than or equal to 0.120 mm.

An outer diameter "Di" of the inner coil 14 is greater than or equal to 0.150 mm and less than or equal to 0.190 mm. The length (total length) Li of the inner coil 14 in the core direction is greater than or equal to 30 mm and less than or equal to 90 mm. In this embodiment, the length (total length) Li of the inner coil 14 is 60 mm. A diameter "di" of the strand 9 of the inner coil 14 is greater than or equal to 0.020 mm and less than or equal to 0.040 mm.

The inner coil 14 comprises a space wound portion (inner space wound portion) 14A on the distal side and a close wound portion (inner close wound portion) 14B on the proximal side. The inner space wound portion 14A is formed on the distal side, from the distal end toward the proximal side. A total length "LiA" of the inner space wound portion 14A is greater than or equal to 4 mm and less than or equal to 12 mm. In this embodiment, the total length "LiA" of the inner space wound portion 14A is 4 mm.

The inner space wound portion 14A is provided in the same position in the core direction as that of the outer space wound portion 13A, in a state that the outer coil 13 and the inner coil 14 are joined to the distal end of the core 11. A coil pitch "Pi" of the inner space wound portion 14A is greater than or equal to 2.0 times the diameter "di" of the strand 9 and less than or equal to 3.50 times the diameter "di" of the strand 9. In this embodiment, the coil pitch "Pi" is approximately 0.075 mm, which is 2.15 times the diameter "di" (0.035 mm) of the strand 9.

According to this embodiment, the strands 8 and 9 are tightened and the diameters of the outer and inner coils 13 and 14 are reduced when the proximal side of the core 11 is rotated in the same direction as the winding direction of the strands 8 and 9 of the outer and inner coils 13 and 14, for example, in the direction of the Z-shaped winding in the case where the strands 8 and 9 are wound into the Z shapes. Thereby the diameters of the outer and inner coils 13 and 14 are reduced simultaneously. The rotation of the proximal side of core 11 in the reverse direction to the winding direction of the strands 8 and 9 loosens the strands 8 and 9. Thereby the outer diameters of the outer and inner coils 13 and 14 increase simultaneously. The simultaneous reduction in the diameters of the outer and inner coils 13 and 14 propels the distal end of guide wire 10 in a stenotic lesion or the like. The simultaneous increase in the diameters of the outer and inner coils 13 and 14 expands or increases the diameter of lesion tissue in the stenotic lesion. Hence, the proximal side of the core 11 is rotated in the same direction as the winding direction of the strands 8 and 9 to reduce the diameters of the outer and inner coils 13 and 14 and thereby the guide wire 10 is propelled forward. The reverse rotation increases the diameters of the outer and inner coils 13 and 14 to radially expand the lesion tissue. The rotation and the reverse rotation are repeated alternately. Thus the capability of the guide wire 10 to pass through the stenotic lesion or a fully occluded lesion is improved significantly.

Note that, in the case where the winding direction of the strand 8 of the outer coil 13 is opposite to the winding direction of the strand 9 of the inner coil 14, the rotation of the proximal side of the core 11 increases the diameter of one of the outer and inner coils 13 and 14 and reduces the diameter of the other, for example, the outer diameter of the inner coil 14 is increased while the outer diameter of the outer coil 13 is reduced. The increase and reduction in diameter occur at the same time and interfere with each other. As a result, the advancement of the guide wire 10, which is caused by the reduction in the diameters of the outer and inner coils 13 and 14, and the expansion of the lesion tissue, which is caused by the increase in the diameters of the outer and inner coils 13 and 14, cannot be performed.

Although the guide wire 10 has a double coil structure, the distal end of the guide wire 10 does not become rigid and is maintained to be flexible by providing the outer space wound portion 13A and the inner space wound portion 14A in the same positions in the core direction. This allows the guide wire 10 to touch vascular walls softly. The guide wire 10 is easily bent in the shape of a letter "J" or an inverted letter "J". Thus the plastic deformation properties of the guide wire 10 are improved.

In the space wound portions 13A and 14A, engagement of the strand 9 of the inner coil 14 with the space "to" between the strands 8 of the outer coil 13 and engagement of the strand 8 of the outer coil 13 with the space "ti" between the strands 9 of the inner coil 14 are prevented by making the coil pitch "Po" of the outer space wound portion 13A different from the coil pitch "Pi" of the inner space wound portion 14A. Otherwise, the engagement partially deforms the distal end portion of the guide wire 10. When the deformation due to the engagement occurs, the guide wire 10 may often become snagged or caught on the lesion tissue in the stenotic lesion or the fully occluded lesion. As a result, it becomes difficult to pass the guide wire 10 through the stenotic lesion or the fully occluded lesion.

The space "to" between the strands 8 of the outer space wound portion 13A is smaller than the diameter "do" of the strand 8. Thereby, in manipulating first and second guide wires in "parallel wire technique", engagement of the strand 8 of the outer coil 13 of the second guide wire, which is inserted subsequent to the first guide wire, with the strand 8 of the outer coil 13 of the first guide wire is prevented. Note that the "parallel wire technique" refers to a procedure to insert a first guide wire into a lesion and then to insert a second guide wire to follow the first guide wire so as to locate a passable vascular path (true lumen) with the second guide wire and pass the second guide wire through an occluded portion. In the case where the space "to" between the strands 8 is greater than the diameter "do" of the strand 8, the strand 8 of one of the first and second guide wires may often engages with the space "to" between the strands 8 of the other guide wire when the second guide wire is inserted to follow the first guide wire. The medical guide wires of the present invention prevent such engagements. The first and second guide wires do not entangle with each other.

(Second Embodiment)

In the guide wire 10 of the first embodiment, the outer diameter of each of the outer coil 13 and the inner coil 14 is constant from the proximal side to the distal side. In a guide wire 20 of the second embodiment, an outer diameter of each of an outer coil 23 and an inner coil 24 gradually tapers from the proximal side to the distal side. Parts other than the above are the same as those in the first embodiment. Like parts have like numerals and the descriptions thereof are omitted.

Figure 3:
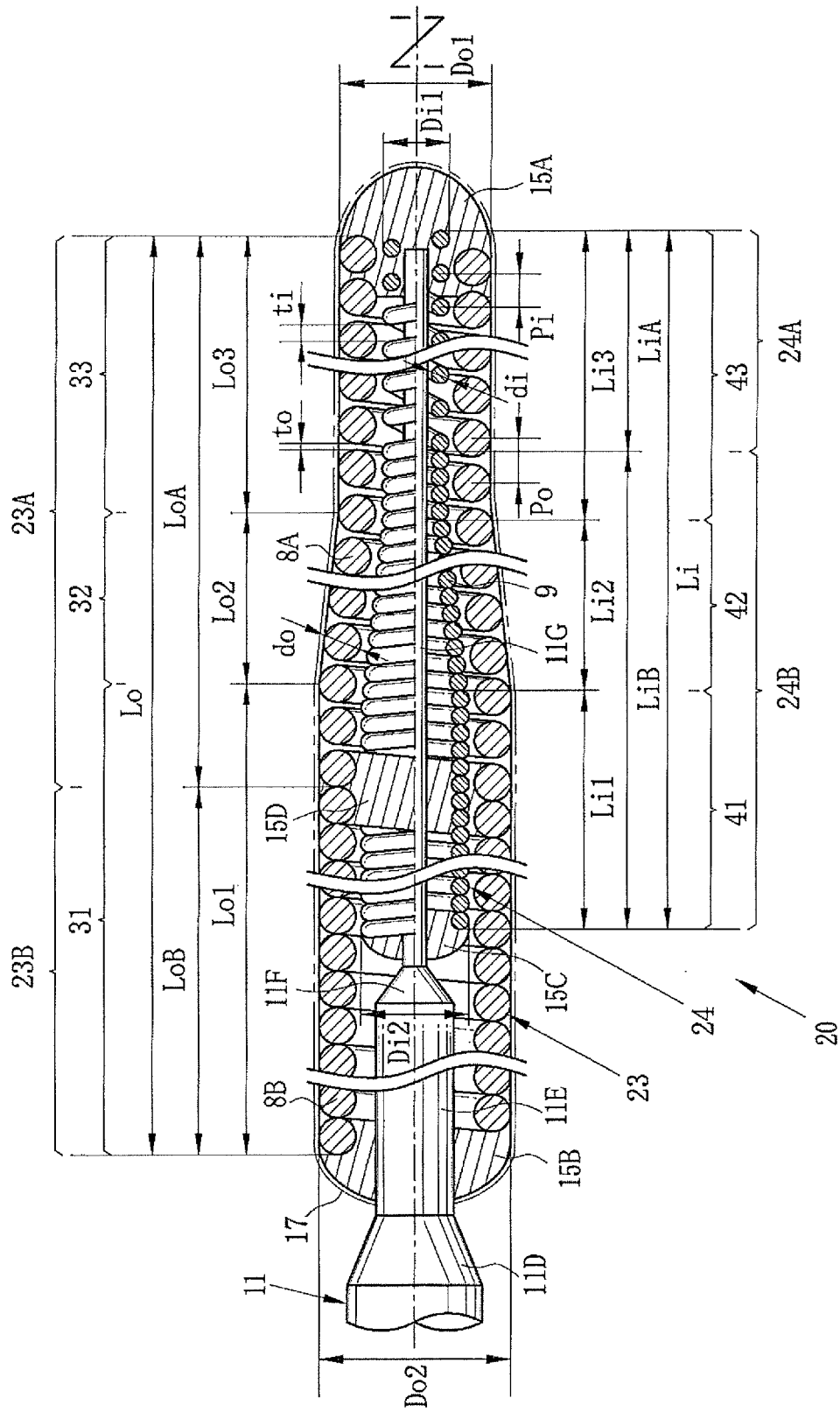
FIG. 3 is a cross-sectional view illustrating dimensions of main parts of the medical guide wire according to a second embodiment.

As shown in FIG. 3, the outer coil 23 comprises a radiopaque outer space wound portion 23A and a radiolucent outer close wound portion 23B which is made from the stainless steel or the like. The outer space wound portion 23A is provided in a region of at least 10 mm, from the inner end of the dome-shaped distal joining section 15A toward the proximal side. Note that a coil pitch "Po" of the outer space wound portion 23A, a space "to" between the strands 8, a diameter "do" of the strand 8, material of the outer coil 23, a cylindrical shape of the outer coil 23 formed by winding at least one strand 8, and the like are the same as those in the first embodiment. The outer space wound portion 23A is joined to the outer close wound portion 23B through the middle joining section 15D in a manner similar to the first embodiment.

The outer coil 23 comprises a large constant diameter portion 31, a tapered middle portion 32, and a small constant diameter portion 33 in this order from the proximal side. The inner coil 24 comprises a large constant diameter portion 41, a tapered middle portion 42, and a small constant diameter portion 43 in this order from the proximal side. To distinguish the portions 31-33 from the portions 41-43, the portions 31-33 of the outer coil 23 are referred to as the outer large constant diameter portion 31, the outer tapered middle portion 32, and the outer small constant diameter portion 33. The portions 41-43 of the inner coil 24 are referred to as the inner large constant diameter portion 41, the inner tapered middle portion 42, and the inner small constant diameter portion 43.

An outer diameter "Do2" of the outer large constant diameter portion 31 is 0.330 mm. An outer diameter of the outer tapered middle portion 32 tapers from 0.330 mm to 0.260 mm. An outer diameter "Do1" of the outer small constant diameter portion 33 is 0.260 mm.

The total length "Lo" of the outer coil 23 is 160 mm. The length "Lo1" of the outer large constant diameter portion 31 is 120 mm. The length "Lo2" of the outer tapered middle portion 32 is 25 mm. The length "Lo3" of the outer small constant diameter portion 33 is 15 mm.

The outer diameter ratio Do2/Do1 between the outer diameter Do2 of the outer large constant diameter portion 31 and the outer diameter Do1 of the outer small constant diameter portion 33 is greater than or equal to 1.10 and less than or equal to 1.50. In the second embodiment, the outer diameter ratio Do2/Do1 is approximately 1.27. In consideration of the maximum outer diameter (0.4572 mm, that is, 0.018 inches) of the guide wire for treatment of lower extremity vessels, the outer diameter ratio Do2/Do1 is greater than or equal to 1.10 and less than or equal to 1.80. In consideration of the guide wire for the cardiovascular treatment and the guide wire for the treatment of lower extremity vessels, the outer diameter ratio Do2/Do1 is greater than or equal to 1.10 and less than or equal to 1.80. and preferably, greater than or equal to 1.15 and less than or equal to 1.80.

Torsional moment on the outer coil 23 is proportionate to the outer diameter ratio Do2/Do1 between the large constant diameter portion 31 and the small constant diameter portion 33. For this reason, the torsional moment from the proximal side to the distal side becomes low when the outer diameter ratio Do2/Do1 is less than the lower limit 1.10. As a result, the guide wire becomes snagged on the lesion tissue in the stenotic portion or the fully occluded lesion and may not be able to pass through it. In the case where the outer diameter ratio Do2/Do1 exceeds the upper limit 1.80. the diameter "di" of the strand 9 needs to be further reduced to reduce an outer diameter "Di1" of the small constant diameter portion 43 of the inner coil 24, which will be described below. The further reduction of the diameter "di" of the strand 9 results in insufficient strength. Hence, in consideration of a body part to be treated, an inner vascular diameter, and practical dimensions of each medical tool used for the radial dilation treatment, the outer diameter ratio Do2/Do1 is greater than or equal to 1.10 and less than or equal to 1.80, and preferably greater than or equal to 1.15 and less than or equal to 1.80.

The inner coil 24 is provided with an inner space wound portion 24A and an inner close wound portion 24B. The inner space wound portion 24A is provided in a region of at least 3 mm, from the inner end of the dome-shaped distal joining section 15A toward the proximal side. The inner close wound portion 24B is provided on the proximal side. The coil pitch "Pi" of the inner space wound portion 24A is 1.5 times to 3.5 times the diameter "di" of the strand 9. In the second embodiment, the diameter "di" of the strand 9 is 0.025 mm and the coil pitch "Pi" is 2.0 times the diameter "di" of the strand 9, so that the coil pitch "Pi" is 0.050 mm. Note that the material of the inner coil 24, the formation of the inner coil 24 by winding at least one strand, and the like are the same as those in the first embodiment.

An outer diameter Di2 of the inner large constant diameter portion 41 is 0.185 mm. An outer diameter of the inner tapered middle portion 42 tapers from 0.185 mm to 0.130 mm. The outer diameter Di1 of the small constant diameter portion 43 is 0.130 mm.

The total length "Li" of the inner coil 24 is 50 mm. The length "Li1" of the inner large constant diameter portion 41 is 15 mm. The length "Li2" of the inner tapered middle portion 42 is 20 mm. The length "Li3" of the inner small constant diameter portion 43 is 15 mm.

The outer diameter ratio Di2/Di1 between the outer diameter Di2 of the inner large constant diameter portion 41 and the outer diameter Di1 of the inner small constant diameter portion 43 is greater than or equal to 1.10 and less than or equal to 1.70. In the second embodiment, the outer diameter ratio Di2/Di1 is approximately 1.42. In consideration of the maximum outer diameter (0.4572 mm, that is, 0.018 inches) of the guide wire for the treatment of lower extremity vessels, the outer diameter ratio Di2/Di1 is greater than or equal to 1.10 and less than or equal to 2.80. In consideration of the maximum outer diameters of the guide wire for the cardiovascular treatment and the guide wire for the treatment of lower extremity vessels, the outer diameter ratio Di2/Di1 is greater than or equal to 1.10 and less than or equal to 2.80. preferably, greater than or equal to 1.15 and less than or equal to 2.75. and more preferably greater than or equal to 1.25 and less than or equal to 2.75.

The torsional moment on the inner coil 24 is proportionate to the outer diameter ratio Di2/Di1 between the inner large constant diameter portion 41 and the inner small constant diameter portion 43. For this reason, the torsional moment from the proximal side to the distal side decreases when the outer diameter ratio Di2/Di1 is less than the lower limit 1.10. As a result, the guide wire becomes snagged on the lesion tissue in the stenotic portion or the fully occluded lesion and may not be able to pass through it. In the case where the outer diameter ratio Di2/Di1 exceeds the upper limit 2.80. torsional resistance of the strand 9, which has a small diameter, becomes insufficient as compared with high torsional moment. The inner coil 24 cannot withstand the high torsional force and starts meandering. As a result, rotation transmission capability of the guide wire to transmit the rotation to the distal side is reduced. Hence, in consideration of a body part to be treated, an inner vascular diameter, and practical dimensions of each medical tool used for the radial dilation treatment, the outer diameter ratio Di2/Di1 is greater than or equal to 1.10 and less than or equal to 2.80, preferably greater than or equal to 1.15 and less than or equal to 2.75. and more preferably greater than or equal to 1.25 and less than or equal to 2.75.

According to the present invention, the outer coil 23 and the inner coil 24 have substantially the same configuration composed of the large constant diameter portion, the tapered middle portion, and the small constant diameter portion. The outer diameter ratio between the large constant diameter portion and the small constant diameter portion is maintained in a given range. The outer diameter ratio of the inner coil is greater than the outer diameter ratio of the outer coil. The length ratio between the close wound portion and the space wound portion of the inner coil in the lengthwise direction is maintained in a given range. Thereby, the rotation transmission capability to transmit the rotation to the distal side is significantly improved. As a result, the selection capability of the guide wire to advance to a desired blood vessel at the blood vessel branch in the lesion and the capability of the guide wire to pass through the lesion are improved.

In the second embodiment, in the case of the cardiovascular treatment, the outer diameter ratio Di2/Di1 of the inner coil 24 is approximately 1.42. The outer diameter ratio Do2/Do1 of the outer coil 23 is approximately 1.27. In consideration of the treatment of lower extremity vessels, the outer diameter Di2 of the large constant diameter portion 41 of the inner coil 24 increases as the outer diameter Do2 of the large constant diameter portion 31 on the proximal side of the outer coil 23 increases from 0.014 inches to 0.018 inches. As a result, the difference between the above-described outer diameter ratios increases. In other words, it is preferable to set the outer diameter ratio Di2/Di1 of the inner coil 24 higher than the outer diameter ratio Do2/Do1 of the outer coil 23.

The reasons for this are described below. The proximal end of the inner coil 24 is joined to the fourth constant diameter portion 11G of the core 11 via the proximal joining section 15C. The diameter of the fourth constant diameter portion 11G is greater than or equal to 0.100 mm and less than or equal to 0.120 mm. The proximal end of the outer coil 23 is joined to the third constant diameter portion 11E of the core 11 via the proximal joining section 15B. The diameter of the third constant diameter portion 11E is greater than or equal to 0.160 mm and less than or equal to 0.190 mm. The diameter of the core 11 to which the inner coil 24 is joined is apparently smaller than the diameter of the core 11 to which the outer coil 23 is joined. When the proximal side of the core 11 with the large diameter is rotated, the torsional moment on the inner coil 24 is lower than that on the outer coil 23 in proportion to the small diameter of the portion of the core 11 to which the inner coil 24 is joined. Hence, the outer diameter ratio of the inner coil 24 is increased to compensate for the reduction in the torsional moment on the inner coil 24. Thus the rotation transmission capability to transmit the rotation to the extreme distal side is further improved.

In the first embodiment, the length ratio LiB/Li between the length "LiB" of the inner close wound portion 24B of the inner coil 24 and the total length "Li" of the inner coil is 0.86. In the second embodiment, the length ratio LiB/Li is 0.94. The length ratio LiB/Li of the length "LiB" of the inner close wound portion 24B to the total length "Li" of the inner coil 24 is greater than or equal to 0.70 and less than or equal to 0.96. preferably greater than or equal to 0.75 and less than or equal to 0.96. and more preferably greater than or equal to 0.80 and less than or equal to 0.96.

The length ratio LiB/Li of the length "LiB" of the inner close wound portion 24B to the total length "Li" of the inner coil 24 is maintained within the above-described range. Thereby a torsion angle decreases in proportion to the length ratio LiB/Li when the proximal side of the core 11 is rotated. The rotation transmission capability is increased by increasing the length ratio LiB/Li and reducing the torsion angle on the proximal side. Thus rotational force is efficiently transmitted from the proximal side to the distal side while the increase in the torsion angle due to the extended inner space wound portion 24A is prevented. Thus the rotation transmission capability is improved.

In order to further improve the rotation transmission capability to transmit the rotation to the distal side, it is preferable to maintain the length ratio LoB/Lo between the length "LoB" of the outer close wound portion 23B and the total length "Lo" of the outer coil 23 within the above-described range, in addition to the length ratio LiB/Li between the length "Lib" of the inner close wound portion 24B and the total length "Li" of the inner coil 24.

In order to easily form the outer space wound portion 23A in the outer coil 23, it is preferable to wind the single strand 8 into a cylindrical shape, rather than winding two or more strands 8 into the cylindrical shape. In order to easily form the inner space wound portion 24A in the inner coil 24, it is preferable to wind the single strand 9 into a cylindrical shape, rather than winding two or more strands 9 into the cylindrical shape. In the case where two or more strands are used for each of the outer space wound portion 23A and the inner space wound portion 24A, the strands need to be wound back in the reverse direction of the winding direction to provide spaces between them. In this case, it is difficult to make the spaces between the strands uniform. In particular, in the case where the brazing member or the like is used to join the strands to the middle portion of the core in the lengthwise direction, it is necessary to make the spaces uniform in the middle portion of the coil, which is extremely difficult. In the case of the coil of the single strand, on the other hand, the space between the strands is set as desired only by applying tension in the lengthwise direction. The space between the strands can be adjusted easily in any portion of the coil such as the end portion or the middle portion.

The outer coil 23 and the inner coil 24 have substantially the same configuration composed of the large constant diameter portion, the tapered middle portion, and the small constant diameter portion from the proximal side to the distal side. The torsional moment is proportionate to the outer diameter ratio between the outer diameter of the large constant diameter portion and the outer diameter of the small constant diameter portion. Hence, the rotation transmission capability to transmit the rotation of the proximal side of the core to the distal side of the core improves with the outer diameter ratio when the outer diameter of the proximal side of the core is increased and the outer diameter of the distal side of the core is reduced. The middle portion has a tapered shape in which the outer diameter gradually decreases toward the distal side. Thereby the middle portion lifts the lesion tissue and improves the capability of the guide wire to pass through the lesion.

The outer diameter ratio between the large constant diameter portion 41 and the small constant diameter portion 43 of the inner coil 24 is greater than or equal to 1.10 and less than or equal to 2.80. The outer diameter ratio between the large constant diameter portion 31 and the small constant diameter portion 33 of the outer coil 23 is greater than or equal to 1.10 and less than or equal to 1.80. The outer diameter ratios are determined in consideration of a body part to be treated with the cardiovascular treatment, the treatment of lower extremity vessels, or the like, an inner vascular diameter, practical dimensions of each tool (a guiding catheter, a balloon catheter, a micro catheter, and the like) used for the radial dilation treatment. With the use of the above-described outer diameter ratios, the guide wire 20 passes through the stenotic portion and the fully occluded lesion without reduction in the torsional moment from the proximal side to the distal side. The high torsional moment does not result in the reduction in the rotation transmission capability to transmit the rotation to the distal side because meandering of a coil which cannot withstand the high torsional moment, in particular, meandering of the small-diameter strand 9 of the inner coil 24 due to insufficient torsional resistance is prevented.

The outer diameter ratio between the large constant diameter portion 41 and the small constant diameter portion 43 of the inner coil 24 is greater than or equal to 1.15 and less than or equal to 2.80. The outer diameter ratio between the large constant diameter portion 31 and the small constant diameter portion 33 of the outer coil 23 is greater than or equal to 1.10 and less than or equal to 1.80. The outer diameter ratio of the inner coil 24 is greater than the outer diameter ratio of the outer coil 23. The outer diameter ratios are determined in consideration of a body part to be treated with the cardiovascular treatment, the treatment of lower extremity vessels, or the like, an inner vascular diameter, practical dimensions of each medical tool (the guiding catheter, the balloon catheter, the micro catheter, or the like) used for the radial dilation treatment. The diameter of the core 11 at the proximal joining section of the inner coil 24 is less than the diameter of the core 11 at the proximal joining section of the outer coil 23. When the proximal side of the core 11 is rotated, the torsional moment on the inner coil 24, which is joined to the small-diameter core 11 (small-diameter portion of the core 11), is lower than the torsional moment on the outer coil 23, which is joined to the large-diameter core 11 (large-diameter portion of the core 11), in accordance with the difference in diameter between the small-diameter and large-diameter portions of the core 11. Hence, the outer diameter ratio of the inner coil 24 is increased to compensate for the reduction in the torsional moment on the inner coil 24. Thus the rotation transmission capability to transmit the rotation to the extreme distal end portion is further improved.

In the inner coil 24, at least each of the large constant diameter portion 41 and the tapered middle portion 42 is composed of the inner close wound portion 24B. At least the distal end of the small constant diameter portion 43 is provided with the inner space wound portion 24A. The ratio of the length "LiB" of the inner close wound portion 24B in the lengthwise direction to the total length "Li" of the inner coil 24 in the lengthwise direction is greater than or equal to 0.70 and less than or equal to 0.96. These ratios are determined in consideration of the flexibility to bend the distal end portion in the shape of the letter "J" or the inverted letter "J", the plastic deformation properties, and the improvement in the rotation transmission capability. Thereby the increase in the torsion angle on the proximal side due to the long space wound portion is prevented when the proximal side of the core is rotated. As a result, the reduction in responsivity on the distal side and reduction in the rotation transmission capability due to the increase in the torsion angle are prevented. The reduction in the flexibility of the distal end portion and the reduction in the plastic deformation properties are also avoided.

The strand 8 of the outer coil 23 and the strand 9 of the inner coil 24 are wound in the same direction as that in the first embodiment. When the proximal side of the core 11 is rotated in the same direction as the winding direction of the strands 8 and 9 of the outer and inner coils 23 and 24, the outer coil 23 and the inner coil 24 are tightened such that the outer diameters of the outer and inner coils 23 and 24 are reduced. Thereby the guide wire 20 advances in the stenotic lesion or the like. When the proximal side of the core 11 is rotated in the reverse direction of the winding direction of the strands 8 and 9, the outer coil 23 and the inner coil 24 are loosened such that the outer diameters of the outer and inner coils 23 and 24 are increased. Thereby the guide wire 20 dilates or expands the lesion tissue in the stenotic lesion or the like. The simultaneous increase and the simultaneous reduction of the diameters of the outer and inner coils 23 and 24 are repeated alternately. Thus the capability of the guide wire to pass through the lesion is significantly improved even in the stenotic lesion or the fully occluded lesion.

The inner space wound portion 24A located at the distal end of the inner coil 24 and the outer space wound portion 23A of the outer coil 23 are provided in the corresponding positions at least in the direction of the core 11. Thereby the flexibility of the distal end of the guide wire is ensured. The capability of the guide wire to bend in the shape of the letter "J" and the plastic deformation properties are improved. The coil pitch of the inner space wound portion 24A of the inner coil 24 differs from the coil pitch of the outer space wound portion 23A of the outer coil 23. Thereby the engagement of the strand 8 with the space is prevented. The space "to" between the strands 8 of the outer space wound portion 23A of the outer coil 23 is less than the diameter of the strand 8. Thereby the engagement of the first and second guide wires with each other is prevented in the parallel wire technique.

Note that the proximal joining section 15C may be provided to the third tapered portion 11F whose outer diameter tapers from 0.120 mm to 0.06 mm toward the distal side. In this case, the inner coil 14 or 24 is joined to the core 11 via the distal joining section 15A and the proximal joining section 15C that is provided to the third tapered portion 11F.

The lengths "LoA" of the outer space wound portions 13A and 23A and the lengths "LoB" of the outer close wound portions 13B and 23B may be changed as necessary. For example, the length of the outer close wound portion 13B, 23B may be greater than or equal to ⅔ of the total length "Lo" of the outer coil 23. The outer space wound portion 23A may be extended and included in the large constant diameter portion 31 or the tapered middle portion 32. In this case, the length "LoA" is preferably less than or equal to 40 mm.

The inner space wound portion 14A and the outer space wound portion 13A may be disposed in the corresponding positions at least in the core direction. The inner space wound portion 24A and the outer space wound portion 23A may be disposed in the corresponding positions at least in the core direction. Hence, the lengths of the inner space wound portions 14A, 24A and the outer space wound portions 13A and 23A in the lengthwise direction may be changed as necessary. The coil pitch "Po" of the outer space wound portion 13A and the coil pitch "Pi" of the inner space wound portion 14A may be gradually increased toward the distal side.

A fourth tapered portion may be provided instead of the second tapered portion 11D, the third constant diameter portion 11E, and the third tapered portion 11F. The outer diameter of the fourth tapered portion tapers from the distal end of the second constant diameter portion 11C toward the proximal end of the fourth constant diameter portion 11G. In this case, the outer coil 13, 23 is joined to the core 11 via the distal joining section 15A and the proximal joining section 15B that is provided to the fourth tapered portion. The inner coil 14, 24 is joined to the core 11 via the distal joining section 15A and the proximal joining section 15C that is provided to the fourth tapered portion.

In the above embodiments, the radiopaque strands 8A which are made from the platinum, the platinum-nickel alloy, the tungsten, or the like are used for the outer space wound portions 13A and 23A. The radiolucent strands 8B which are made from stainless steel or the like are used for the outer close wound portions 13B and 23B. Alternatively, the radiopaque strands 8A and 8B which are made from the platinum, the platinum-nickel alloy, the tungsten, or the like may be used for the outer space wound portions 13A and 23A and the outer close wound portions 13B and 23B.

Various changes and modifications are possible in the present invention and may be understood to be within the present invention.

What is claimed is:

1. A medical guide wire comprising:
a core having a large diameter on a proximal side and being tapered in diameter on a distal side toward a core distal end tip, wherein a core distal end portion spans from a point where the core begins to taper from the large diameter on the proximal side to the core distal end tip;
an inner coil formed by helically winding at least one strand, a coil distal end of the inner coil being joined to the core distal end tip on an outer periphery of the core distal end portion of the core, a coil proximal end of the inner coil being joined to the core in the core distal end portion;
an outer coil formed by helically winding at least one strand and located outside of the inner coil, the outer coil being longer than the inner coil in a direction of the core, a coil distal end of the outer coil being joined to the core distal end tip and a coil proximal end of the outer coil being joined to the core in the core distal end portion;
an inner spaced coil winding portion provided on a distal side of the inner coil, a coil pitch of the inner spaced coil winding portion including a first space between adjacent helical windings of the inner coil;
an outer spaced coil winding portion provided in the outer coil located outside of the inner spaced coil winding portion, a coil pitch of the outer spaced coil winding portion including a second space between adjacent helical windings of the outer coil, said second space differing from the first space of the coil pitch of the inner spaced coil winding portion;
wherein the inner coil has a large constant diameter portion, a tapered middle portion, and a small constant diameter portion from the proximal side to the distal side and the outer coil has a large constant diameter portion, a tapered middle portion, and a small constant diameter portion from the proximal side to the distal side;
the inner and outer spaced coil winding portions are provided in coil distal end portions of the small constant diameter portions, respectively of the inner and outer coils; and
an outer diameter ratio (Di2/Di1) of the inner coil is greater than or equal to 1.15 and less than or equal to 2.80 and an outer diameter ratio (Do2/Do1) of the outer coil is greater than or equal to 1.10 and less than or equal to 1.80 and the outer diameter ratio (Di2/Di1) of the inner coil is greater than the outer diameter ratio (Do2/Do1) of the outer coil {(Di2/Di 1)>(Do2/Do1)} where Di1 denotes an outer diameter of the small constant diameter portion of the inner coil, Di2 denotes an outer diameter of the large constant diameter portion of the inner coil, Do1 denotes an outer diameter of the small constant diameter portion of the outer coil, and Do2 denotes an outer diameter of the large constant diameter portion of the outer coil.

2. The medical guide wire according to claim 1, wherein a winding direction of the strand of the inner coil is the same as a winding direction of the strand of the outer coil.

3. The medical guide wire according to claim 1, wherein the coil pitch of the inner spaced coil winding portion is greater than or equal to 2.00 times a diameter of the strand and less than or equal to 3.50 times the diameter of the strand and the coil pitch of the outer spaced coil winding portion is greater than or equal to 1.20 times a diameter of the strand and less than or equal to 1.90 times the diameter of the strand.

4. The medical guide wire according to claim 1, wherein
- at least the large constant diameter portion and the tapered middle portion of the inner coil are close winding portions, in each of which the strands are in contact with each other, and
- a length ratio (LiB/Li) is greater than or equal to 0.70 and less than or equal to 0.96 where Li denotes a total length of the inner coil and LiB denotes a length of the close winding portion.

* * * * *